United States Patent [19]

Arnold

[11] Patent Number: 4,560,504
[45] Date of Patent: Dec. 24, 1985

[54] CARBOXYL ANCHORED IMMOBILIZED ANTIBODIES

[75] Inventor: Edward C. Arnold, Naperville, Ill.

[73] Assignee: UOP Inc., Des Plaines, Ill.

[21] Appl. No.: 678,953

[22] Filed: Dec. 6, 1984

[51] Int. Cl.[4] .................. A61K 39/44; C07G 7/00; C07G 7/04
[52] U.S. Cl. ..................... 260/112 B; 260/112 R; 424/85; 435/172.2; 435/240; 435/241; 435/948; 436/548
[58] Field of Search ............... 435/7, 180, 181, 188, 435/172.2, 240, 241, 948; 260/112 B, 112 R; 424/85; 436/548

[56] References Cited

U.S. PATENT DOCUMENTS

| 4,140,662 | 2/1979 | Reckel et al. | 260/112 R X |
| 4,141,857 | 2/1979 | Levy et al. | 252/430 |
| 4,260,678 | 4/1981 | Lepp et al. | 435/7 |
| 4,284,553 | 8/1981 | Brown et al. | 260/112 R |
| 4,347,312 | 8/1982 | Brown et al. | 435/7 |
| 4,357,311 | 11/1982 | Schutt | 435/7 X |
| 4,361,509 | 11/1982 | Zimmerman et al. | 260/112 B |
| 4,381,291 | 4/1983 | Ekins | 436/500 X |
| 4,399,217 | 8/1983 | Holmquist et al. | 435/7 |

OTHER PUBLICATIONS

Methods Enzymol. 44 (1976), pp. 138–148, Mossbach.

Primary Examiner—Howard E. Schain
Attorney, Agent, or Firm—Thomas K. McBride; William H. Page II; Eugene I. Snyder

[57] ABSTRACT

An immobilized antibody system can be made by reacting an aminated core support with an antibody in the presence of a condensing agent which promotes the formation of the amide linkage. The immobilized antibody system is highly resistant to leaching, may be made incompressible, sterilizable, and pyrogen-free. Such an immobilized antibody system is well suited for repeated use with minimal change in its physical and biochemical properties.

17 Claims, No Drawings

CARBOXYL ANCHORED IMMOBILIZED ANTIBODIES

BACKGROUND OF THE INVENTION

The emergence of antibodies, especially immobilized antibodies, as an article of commerce is an area whose continued expansion is virtually assured. Commercial uses rarely require the free antibody, but instead require the antibody bound to some insoluble substrate. This application relates to immobilized antibodies; more particularly, it relates to immobilized antibodies, especially immobilized monoclonal antibodies, intended for repeated commercial use.

Although the area of immobilized antibodies may seem analogous to the relatively well developed area of immobilized enzymes, the requirements and preparation of the two are not congruent. In particular, because an immobilized antibody may be used in a sterile and pyrogen-free environment, one of its requirements is that the underlying support matrix be capable of withstanding sterilization and depyrogenation procedures without affecting its ability to bind antibodies or the activity of the bound antibody. Since the antibody to be immobilized often is quite expensive it is also paramount that the immobilized antibody be capable of repeated use, leading to the second requirement that the antibody be covalently bound to the underlying support matrix. Another aspect of the efficient use of an antibody is the requirement that it exhibit activity and specificity when immobilized comparable to that manifested in solution, which leads to two derivative requirements. One is that the support to which the antibody is bound be chemically and biochemically inert as regards the antibody, the substrate, and other solution components in the environment of the process where used. The second derivative requirement is that the antibody be immobilized to the extent possible with both of its active (affinity) sites oriented away from the support, which provides for effective utilization of the antibody by allowing unhindered access of antigen to antibody. It is also important that the support components, binding agents, and antibody do not dissolve, wash off, or dissociate to any degree that might cause an immune response to these materials during subsequent use of the purified antigen. Lastly, the desire for a fixed bed process (or fluidized bed and similar processes) with a high linear velocity requires that the underlying matrix be noncompressible and attrition resistant.

We have discovered that an immobilized antibody system comprised of an aminated core support with an antibody covalently bonded thereto via amide linkages formed between the amino groups of the support and the carboxylic acid groups of the antibody, especially where the affinity sites of the antibody are oriented away from the support, meets all the aforementioned requirements. Therefore, such a system is highly advantageous in its field of intended use. Although the underlying support matrix is distantly related to that of U.S. Pat. No. 4,141,857, its application to a polypeptide or proteinaceous material by formation of amide linkages is hitherto neither disclosed nor appreciated, especially in the context of the aforementioned requirements.

Covalently bonded, immobilized antibodies are amply exemplified in the prior art. U.S. Pat. No. 4,399,217 relates to an immobilized antibody covalently bonded via diazo groups originating from diazotized poly(aminostyrene). U.S. Pat. No. 4,381,291 exemplifies covalent bonding of an antibody to a cyanogen bromide activated microcrystalline cellulose. In U.S. Pat. No. 4,357,311 there is described an antibody covalently bonded to trichloro-s-triazene activated microporous cellulose esters. In U.S. Pat. No. 4,347,312 the patentee immobilized antibodies by covalently bonding them to acylated aminopropylsilylated glass. U.S. Pat. No. 4,260,678 broadly discloses immobilization of antibodies, including the use of metal oxides as inorganic carriers. However, it is essential to recognize that all of the aforementioned art, which is exemplary only, relate solely to single use utilization, i.e., the immobilized antibody is used in a single immunochemical determination and then discarded. Furthermore, such art relate only to antibodies coupled in non-specific orientations, and do not teach sterilizability or nonpyrogenicity of the activated support. Hence, such art is of questionable relevance to the subject matter here where the repeated use of an immobilized antibody, preferably sterile and pyrogen-free, with little or no diminution of activity is an essential requirement.

In U.S. Pat. No. 4,361,509 the patentee coupled a monoclonal antibody in a non-specific orientation to a cyanogen bromide activated, crosslinked agarose to afford a column used in affinity chromatography. Arguably, this exemplifies a multiple or repeated use of a covalently bonded immobilized antibody but fails to address other features mentioned in the preceding paragraph.

SUMMARY OF THE INVENTION

The object of this invention is to prepare a stable, nonleachable, high efficiency immobilized antibody system where the underlying support is chemically inert, macroporous, of high surface area, incompressible, capable of being made pyrogen-free and sterilizable. An embodiment comprises a porous or semi-porous solid aminated core support whose amino groups are covalently bonded via an amide linkage to carboxylic acid groups of an antibody or fragment thereof. In a more specific embodiment, alumina impregnated with polyethyleneimine, optionally crosslinked, is the core support, and the antibody is a monoclonal antibody. In another embodiment a substantial portion of the antibody is bound in a specific orientation with its affinity sites directed away from the support, i.e., with both affinity groups exposed.

DESCRIPTION OF THE INVENTION

This invention is based on the discovery that an immobilized antibody system comprising an aminated porous or semi-porous solid as a core support which is subsequently reacted with the carboxylic acid groups of an antibody so as to form a covalent amide linkage, is a system capable of repeated or continual use without substantial physical loss of antibody via leaching, and without loss of activity via denaturation or other physical or chemical degradation often attending a single use or a short interval of continued use of other immobilized antibody systems, even when the underlying support matrix is sterilized, or dried, or treated to make it pyrogen-free.

The underlying support or carrier of the system is an aminated porous or semi-porous solid. In one branch of this invention the core support is an aminated inorganic material; in another branch the support is an aminofunctionalized polyhydroxylic organic material. Both branches manifest the same, unifying, underlying characteristic of bearing a multitude of amino groups which can react with carboxylic acid groups of an antibody to form covalent amide linkages.

In that branch of this invention where the core support is an aminated inorganic solid, the materials which may be used include the aluminas, silica, silica-alumina, zirconia, silica-zirconia-alumina, magnesia, titania, porous glass, charcoal in any suitable form, diatomaceous earth, and any combination of the above. Alumina is an especially desirable carrier, particularly gamma-alumina, alpha-alumina, and theta-alumina. All of these carriers may be prepared so as to make them sterile and pyrogen-free.

The inorganic solid is then aminated, either by impregnation with a polyamine or reaction with an amino-containing reagent, such as an aminoalkylsilane. Among the polyamines which are suitable in the practice of this invention are poly(ethyleneamines), such as ethylenediamine, diethylenetriamine, triethylenetetramine, tetraethylenepentamine, pentaethylenehexamine, and polyethyleneimine. Other examples of polyamines include hexamethylenetetramine, phenylenediamine, and epiamines. For the purpose of this invention an epiamine is the reaction product of poly(epichlorohydrin) with an alkylenediamine containing from 2 to about 10 carbon atoms.

Impregnation may be performed by any suitable means. For example, one suitable means is to contact a solution containing the desired amount of polyamine with the carrier with mixing and removing the solvent by evaporation. Generally, aqueous solutions of the polyamine are used, but if the polyamine is insoluble, or only sparingly soluble, in water a partly aqueous or even nonaqueous solvent may be used advantageously. Like the inorganic oxide, the polyamine may be prepared so as to make it pyrogen-free.

The polyamine impregnated inorganic solid optionally may be reacted with a polyfunctional reagent to crosslink the polyamine, thereby securing it more effectively to the inorganic oxide. It is to be noted that only enough polyfunctional reagent to crosslink most or some portion of the polyamine is used, which is equivalent to an amount from about 0.05 up to about 1 molar proportion of polyfunctional reagent, although a maximum of about 0.5 molar proportion is more usual. The polyfunctional reagent also may be treated to make it pyrogen-free.

Among the polyfunctional reagents which may be used are included dialdehydes of formula $OHC(CH_2)_n\text{-}CHO$, dicarboxylic acid halides of formula $XOC(CH_2)_nCOX$ where X is a halogen, especially chlorine or bromine, and diisocyanates of formula $OCN(CH_2)_n\text{-}NCO$, where n is an integer from 2 to about 10. Aromatic dialdehydes and diisocyanates, such as phthalaldehyde and toluene diisocyanate, resp., also may be used. Reaction of the polyamine impregnated oxide with the polyfunctional reagent usually occurs merely by mixing the two for several hours at or about room temperature. Where the polyfunctional reagent is adequately soluble in water its aqueous solution is used, otherwise its solution in an unreactive organic solvent is used. Solutions up to about 10% by weight of the polyfunctional reagent may be employed although normally the solutions are on the order of 0.005 to about 0.5%. The polyfunctional reagent may also be prepared pyrogen-free.

When the reaction between the polyamine and polyfunctional reagent is complete, excess solution of the reagent is removed, as by decantation, and the solid is then washed with copious quantities of whatever solvent was used for the polyfunctional reagent so as to remove adhering but unreacted reagent. The resulting carrier coated with a polyamine crosslinked with an agent may be dried and stored, autoclaved or irradiated and stored, or may be reacted immediately with a suitable antibody.

In a variant of this invention an inorganic oxide is reacted with an amino-bearing reagent so as to furnish the resulting aminated core support. The most common method of achieving this is by introducing an $\omega$-aminoalkylsilyl group by an appropriate silylating agent, especially where glass is used as the inorganic oxide. Examples of aminoalkylsilyl groups thus introduced include $\beta$-aminoethylsilyl, $\gamma$-aminopropylsily, $\delta$-aminobutylsilyl, and so on. The corresponding silylating agents are well known and include the silyl halides and silyl ethers.

In another branch of this invention the core support is an amino-functionalized polyhydroxylic organic material. Examples of the latter include aminoethyl-cellulose, chitosan (the deacetylated product of chitin), and $\omega$-aminoalkylsilylated products of cellulose, starch and other polysaccharides generally.

The aminated core support prepared according to the aforementioned description is then contacted with an aqueous solution of an antibody or antibody fragment in the presence of a condensing agent which promotes formation of an amide linkage so as to bind the antibody or antibody fragment to the matrix. As previously mentioned, reaction occurs between an amino group of the core support and a carboxylic acid group of the antibody with formation of an amide linkage, thereby affording a covalent attachment between the support and antibody. The condensing agent used is a dehydrating agent specifically promoting formation of the amide linkage and is one such as is commonly used in peptide synthesis. Examples of such condensing agents include carbodiimides, especially N,N'-dicyclohexyl carbodiimide, 1-ethyl-3-(3-dimethylaminopropyl)carbodiimide hydrochloride, 1-cyclohexyl-3-(2-motpholinoethyl)carbodiimide metho-p-toluenesulfonate, N-ethyl-5-phenylisoxazolium-3'-sulfonate, and N-ethoxycarbonyl-2-ethoxy-1,2-dihydroquinoline.

In a preferred embodiment the antibody or antibody fragment is covalently bound to the matrix in a specific orientation so as to leave its affinity sites unbonded and oriented away from the surface. This may be achieved by first forming the complex of the antibody, or antibody fragment, with its antigen, a fragment of said antigen, or an analogue of the antigen, which then hinders covalent bonding of the carboxylic acid groups, if any, of the antibody near its affinity site. Binding the antibody in the complex followed by decoupling or removal of the antigen, antigen fragment or analog, such as by changing pH, ionic strength, temperature, and so forth then gives a bound antibody whose affinity sites tend to be oriented away from the surface of the matrix, i.e., both affinity groups are exposed. It needs to be explicitly understood that using antigens or antigen fragments with free carboxylic acid groups is to be avoided during the immobilization procedure, as these will compete with like groups of the antibody in covalent bonding to the support.

The antibody may be a polyclonal or monoclonal antibody, with monoclonal antibodies being favored. Among the antibodies which may be used are included the $I_gA$, $I_gE$, $I_gG$, or $I_gM$ immunoglobulins. Reaction between the antibody and the matrix generally is complete in an interval between about 4 and about 24 hours at a temperature between 4° and about 25° C. The resulting immobilized antibody system is then washed with copious quantities of water, buffer solution, or salt solution to remove all adhering but unbound and unreacted materials from the immobilized antibody system.

It also may be desirable to limit the amount of antibody bound to the support while still covering the entire support surface with inert protein or similar polymeric materials in order to eliminate non-specific binding of protein during the purification procedure. This may be achieved by mixing with the antibody, prior to its contact with an activated support, an inert protein, or polypeptide, i.e., one having no antibody characteristics. Both the inert protein and the antibody would bind to the support in a ratio approximately equal to their ratio in solution. Among the materials which may be so utilized are bovine serum albumin and polyglycine.

The immobilized antibody system so prepared may be utilized in a variety of ways. For example, it may be one reagent in an immunochemical analysis kit capable of repeated reuse. Another example is its use as a cleansing filter for extracorporeal treatment of blood or for purification of plasma. Alternatively, the immobilized antibody system may be used as the adsorbent in a process based on affinity chromatography. The varied uses of an immobilized antibody system are well known to those in the art and need not be further discussed here. Those cited above are but exemplary and illustrative and are by no means exhaustive.

The example given below is merely illustrative of this invention and is not intended to limit it thereto.

EXAMPLE

Particulate theta-alumina (60×80 mesh) is prepared pyrogen-free, that is, free of all gram-negative bacteria and their lipopolysaccharide byproducts. Handling of the support in all its forms during subsequent treatment is done so as to maintain the pyrogen-free state. Using sterile techniques, the alumina may be mixed with an aqueous solution of polyethylenimine treated so as to make it sterile and pyrogen-free. The polyethylenimine may be added at a level of about 90 mg per gram of support. Excess solution of polyethylenimine may be decanted from the theta-alumina and the residual liquid removed using vacuum evaporation.

The polyethylenimine coated support then may be mixed with an aqueous solution of sterile, pyrogen-free glutaraldehyde at a concentration of 0.3 wt. % and in an amount to afford about 30 ml. of solution per gram of volatile-free base. After about ten minutes, the excess glutaraldehyde solution is decanted and the activated support is then washed with sterile, pyrogen-free 0.85 wt. % saline solution at pH 7.0 and 4° C. for 30 minutes. The activated support in saline solution is then autoclaved for 30 minutes at 121° C. and stored at room temperature until ready for use.

Monoclonal antibody to insulin may be made using the method developed by Milstein and Kohler, Nature, 256, 495-7. A hydridoma producing a "medium affinity" antibody may be selected for immobilization purposes. A portion of the insulin monoclonal antibody may be combined with insulin in an aqueous 0.85 wt. % saline solution at a pH of 6.5 and at 4° C. An aqueous slurry of the activated support described above may be adjusted to pH between about 3.7 and 4.9 with hydrochloric acid, and a portion of the insulin antibody-insulin solution is added to this slurry at an offering of 0.050 grams antibody per gram of support. Bovine serum albumin then may be added to the above slurry at an offering of approximately 0.2 grams albumin per gram of support. Coupling of the carboxyl groups of the antibody to the amino groups of the support is effected by adding to the stirred slurry a solution of 1-ethyl-3-(3-dimethylaminopropyl)carbodiimide hydrochloride at a level of about 0.015 grams carbodimide per gram of support. The pH of the slurry may be immediately adjusted to a pH from about 3.7 to about 4.9 and the slurry may be kept at a temperature from about 4° to about 25° C. for about two hours.

The resulting immobilized antibody system may then be washed with about 20 bed volumes of a pyrogen-free, sterile, 0.85 wt. % saline solution at a pH of 6.5 and a temperature of about 4° C. to wash off unbound monoclonal antibody and bovine serum albumin. The system then may be washed with about 20 bed volumes of sterile, pyrogen-free, 0.85 wt. % saline solution at a pH between 3.5 and about 4.5 to decouple the insulin. Finally, the immobilized monoclonal antibody may be stored in a sterile, pyrogen-free 0.85 wt. % saline solution.

What is claimed is:

1. An immobilized antibody system comprising an aminated core support, selected from the group consisting of porous or semi-porous inorganic solids containing amino groups and amino-functionalized polyhydroxylic organic materials, and an antibody or antibody fragment covalently bonded to the support by an amide linkage resulting from the reaction of an amino group of the core support with a carboxylic acid group of the antibody.

2. The immobilized antibody system of claim 1 where the core support is a porous or semi-porous inorganic solid selected from the group consisting of alumina, silica-alumina, zirconia, silica-zirconia-alumina, magnesia, titania, porous glass, charcoal, diatomaceous earth, and any combination of the above, containing amino groups from aminosilylation or impregnation with a polyamine.

3. The immobilized antibody system of claim 2 where the polyamine is selected from the group consisting of ethylenediamine, diethylenetriamine, triethylenetetramine, tetraethylenepentamine, pentaethylenehexamine, polyethyleneimine, hexamethylenetetramine, phenylenediamine, and epiamines.

4. The immobilized antibody system of claim 1 where the polyhydroxylic organic material is selected from the group consisting of aminoethylcellulose, chitosan, and aminosilylated polysaccharides.

5. The immobilized antibody system of claim 2 where the polyamine is crosslinked.

6. The immobilized antibody system of claim 1 where the antibody is immobilized in a specific orientation with both of its affinity groups exposed.

7. The immobilized antibody system of claim 1 where the antibody or antibody fragment is a monoclonal antibody or antibody fragment.

8. The immobilized antibody system of claim 7 where the antibody is a type $I_gA$, $I_gE$, $I_gM$, or $I_gG$ immunoglobulin.

9. A method of preparing an immobilized antibody system comprising reacting an aminated core support, selected from the group consisting of porous or semi-porous inorganic solids containing amino groups and amino-functionalized polyhydroxylic organic materials, with an antibody in the presence of a condensing agent which promotes formation of an amide linkage, and recovering the resulting immobilized antibody system.

10. The method of claim 9 where the core support is a porous or semi-porous inorganic solid selected from the group consisting of alumina, silica-alumina, zirconia, silica-zirconia-alumina, magnesia, titania, porous glass, charcoal, diatomaceous earth, and any combination of the above, containing amino groups from aminosilylation or impregnation with a polyamine.

11. The method of claim 10 where the polyamine is selected from the group consisting of ethylenediamine, diethylenetriamine, triethylenetetramine, tetraethylenepentamine, pentaethylenehexamine, polyethyleneimine, hexamethylenetetramine, phenylenediamine, and epiamines.

12. The method of claim 9 where the polyhydroxylic organic material is selected from the group consisting of aminoethylcelulose, chitosan, and aminosilylated polysaccharides.

13. The method of claim 10 where the polyamine is crosslinked.

14. The method of claim 9 where the antibody is immobilized in a specific orientation with both of its affinity groups exposed.

15. The method of claim 9 where the antibody is a monoclonal antibody.

16. The method of claim 15 where the antibody is a type $I_gA$, $I_gE$, $I_gM$, or $I_gG$ immunoglobulin.

17. The method of claim 9 where the condensing agent is selected from the group consisting of N,N'-dicydohexylcarbodiimide, 1-ethyl-3-(3-dimethylaminopropyl)carbodiimide hydrochloride, 1-cyclohexyl-3-(2-morpholinoethyl)carbodiimide metho-p-toluenesulfonate, N-ethyl-5-phenyl-isoxazolium-3'-sulfonate, and N-ethoxycarbonyl-2-ethoxy-1,2-dihydroquinoline.

* * * * *